United States Patent
Hamilton et al.

(10) Patent No.: US 11,719,778 B1
(45) Date of Patent: Aug. 8, 2023

(54) MULTICONTRAST SYNTHETIC LATE GADOLINIUM ENHANCEMENT IMAGING USING POST-CONTRAST MAGNETIC RESONANCE FINGERPRINTING

(71) Applicants: REGENTS OF THE UNIVERSITY OF MICHIGAN, Ann Arbor, MI (US); CASE WESTERN RESERVE UNIVERSITY, Cleveland, OH (US); UNIVERSITY HOSPITALS CLEVELAND MEDICAL CENTER, Cleveland, OH (US)

(72) Inventors: Jesse Hamilton, Ann Arbor, MI (US); Imran Rashid, Cleveland, OH (US); Nicole Seiberlich, Ann Arbor, MI (US); Sanjay Rajagopalan, Cleveland, OH (US)

(73) Assignees: REGENTS OF THE UNIVERSITY OF MICHIGAN, Ann Arbor, MI (US); CASE WESTERN RESERVE UNIVERSITY, Cleveland, OH (US); UNIVERSITY HOSPITALS CLEVELAND MEDICAL CENTER, Cleveland, OH (US)

( * ) Notice: Subject to any disclaimer, the term of this patent is extended or adjusted under 35 U.S.C. 154(b) by 0 days.

(21) Appl. No.: 17/589,780

(22) Filed: Jan. 31, 2022

(51) Int. Cl.
*G01R 33/56* (2006.01)
*G01R 33/50* (2006.01)
(Continued)

(52) U.S. Cl.
CPC ........ *G01R 33/5608* (2013.01); *A61B 5/0044* (2013.01); *A61B 5/055* (2013.01); *G01R 33/483* (2013.01); *G01R 33/50* (2013.01)

(58) Field of Classification Search
CPC .... A61B 5/055; A61B 5/0044; G01R 33/483; G01R 33/50; G01R 33/5608
See application file for complete search history.

(56) References Cited

U.S. PATENT DOCUMENTS

| | | | |
|---|---|---|---|
| 2013/0266203 A1* | 10/2013 | Geerts-Ossevoort | G01R 33/5635 382/131 |
| 2017/0074959 A1* | 3/2017 | Li | G01R 33/5676 |

OTHER PUBLICATIONS

Kellman, Peter, et al. "Bright-Blood and Dark-Blood Phase Sensitive Inversion Recovery Late Gadolinium Enhancement and T1 and T2 Maps in a Single Free-Breathing Scan: An All-in-One Approach." Journal of Cardiovascular Magnetic Resonance, vol. 23, No. 1, 2021 (Year: 2021).*

(Continued)

*Primary Examiner* — Gregory H Curran
(74) *Attorney, Agent, or Firm* — Marshall, Gerstein & Borun LLP

(57) ABSTRACT

Methods and systems generate synthetic late gadolinium enhancement (LGE) magnetic resonance images using a magnetic resonance fingerprinting (MRF) acquisition. From a single acquisition, MRF image data is obtained, including co-registered $T_1$ and $T_2$ tissue property maps. Different tissue regions of interest are identified, such as viable myocardium, scar, and blood and $T_1$ and $T_2$ values for each are determined. Based on these, different sets of pulse sequence parameters are determined, e.g., using different synthetic image contrast models receiving the MRF image data. Synthetic LGE images at different contrasts are generated as a result, including a synthetic bright-blood LGE image, a synthetic dark-blood/gray-blood LGE image, and a synthetic optimized imaged.

22 Claims, 10 Drawing Sheets
(6 of 10 Drawing Sheet(s) Filed in Color)

(51) Int. Cl.
    A61B 5/00     (2006.01)
    A61B 5/055    (2006.01)
    G01R 33/483   (2006.01)

(56) References Cited

OTHER PUBLICATIONS

Hamilton, Jesse I., et al. "MR Fingerprinting for Rapid Quantification of Myocardial T1, T2, and Proton Spin Density." Magnetic Resonance in Medicine, vol. 77, No. 4, 2016, pp. 1446-1458., https://doi.org/10.1002/mrm.26216. (Year: 2016).*
Abdula et al. Synthetic late gadolinium enhancement cardiac magnetic resonance for diagnosing myocardial scar. Scand Cardiovasc J. 2018;52(3):127-132.
Basha et al., Black blood late gadolinium enhancement using combined T(2) magnetization preparation and inversion recovery. In: Journal of Cardiovascular Magnetic Resonance. vol 17. ; 2015:O14.
Gupta et al., Myocardial infarction: optimization of inversion times at delayed contrast-enhanced MR imaging. Radiology. 2004;233(3):921-926.
Holtackers et al., Dark-blood late gadolinium enhancement without additional magnetization preparation. J Cardiovasc Magn Reson Off J Soc Cardiovasc Magn Reson. 2017;19(1):64.
Kellman et al. Dark blood late enhancement imaging. J Cardiovasc Magn Reson Off J Soc Cardiovasc Magn Reson. 2016;18(1):77.
Kellman et al., Phase-sensitive inversion recovery for detecting myocardial infarction using gadolinium-delayed hyperenhancement. Magn Reson Med. 2002;47(2):372-383.
Kim et al. Dark-Blood Delayed Enhancement Cardiac Magnetic Resonance of Myocardial Infarction. JACC Cardiovasc Imaging. 2018;11(12):1758-1769.
Kim et al., How we perform delayed enhancement imaging. J Cardiovasc Magn Reson Off J Soc Cardiovasc Magn Reson. 2003;5(3):505-514.
Kim et al., Myocardial Gd-DTPA kinetics determine MRI contrast enhancement and reflect the extent and severity of myocardial injury after acute reperfused infarction. Circulation. 1996;94(12):3318-3326.
Leiner et al. SCMR Position Paper (2020) on clinical indications for cardiovascular magnetic resonance. J Cardiovasc Magn Reson Off J Soc Cardiovasc Magn Reson. 2020;22(1):76.
Lima da Cruz et al., Sparsity and locally low rank regularization for MR fingerprinting. Magn Reson Med. 2019;81(6):3530-3543.
Ma et al., Magnetic resonance fingerprinting, Nature. 2013;495(7440):187-192.
McGivney et al. SVD compression for magnetic resonance fingerprinting in the time domain. IEEE Trans Med Imaging. 2014;33(12):2311-2322.
Muscogiuri et al. T(Rho) and magnetization transfer and INvErsion recovery (TRAMINER)-prepared imaging: A novel contrast-enhanced flow-independent dark-blood technique for the evaluation of myocardial late gadolinium enhancement in patients with myocardial infarction. J Magn Reson Imaging. 2017;45(5):1429-1437.
Simonetti et al. An improved MR imaging technique for the visualization of myocardial infarction. Radiology. 2001;218(1):215-223.
Varga-Szemes et al. Effect of inversion time on the precision of myocardial late gadolinium enhancement quantification evaluated with synthetic inversion recovery MR imaging. Eur Radiol. 2017;27(8):3235-3243.
Varga-Szemes et al. Myocardial Late Gadolinium Enhancement: Accuracy of T1 Mapping-based Synthetic Inversion-Recovery Imaging. Radiology. 2016;278(2):374-382.

* cited by examiner

MULTICONTRAST SYNTHETIC LATE GADOLINIUM ENHANCEMENT IMAGING USING POST-CONTRAST MAGNETIC RESONANCE FINGERPRINTING

FIELD OF THE DISCLOSURE

The invention generally relates to magnetic resonance fingerprinting techniques and, more particularly, to generating synthetic MRI contrast images using magnetic resonance fingerprinting techniques.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Late gadolinium enhancement (LGE) magnetic resonance imaging (MRI) is a non-invasive reference standard for imaging of myocardial scar and fibrosis. In this technique, images are acquired several minutes after injection of a gadolinium-based contrast agent using a $T_1$-weighted inversion recovery sequence. The inversion time (TI) is selected to null signal from viable myocardium so that scar and fibrosis appear bright in the LGE MRI image. Although LGE MRI has high sensitivity and specificity for detection of ischemic and nonischemic cardiomyopathy, conventional LGE methods are time-consuming, and the image quality is operator dependent. The scan operator must manually choose the TI that best nulls viable myocardium, often by acquiring a TI scout scan before the LGE scan. Suboptimal TI selection leads to inadequate image quality and decreased sensitivity for scar and fibrosis. Furthermore, the optimal TI changes over time due to contrast agent washout, requiring the scan operator to increase the TI every few minutes.

Another limitation of conventional bright-blood LGE is potential difficulty in distinguishing subendocardial scar from blood due to their similar signal intensities. Dark-blood LGE sequences provide improved contrast between scar and blood and have been proposed using $T_2$, magnetization transfer, and $T_1$-rho prepared sequences. Disadvantages of dark-blood LGE include the need for specialized sequences, lower signal-to-noise ratio (SNR), and operator-dependent selection of parameters (which is more complex for dark-blood imaging due to the larger number of tunable parameters).

While acquiring both bright-blood and dark-blood LGE in images in the same patient may allow better delineation of scars by combining the advantages of each technique (e.g., high contrast between viable myocardium and scar on bright-blood LGE, and high contrast between blood and scar on dark-blood LGE), using conventional methods, this would require multiple acquisitions and that may not be feasible during the limited time window before contrast washout.

There has been recent interest in synthetic LGE, which simulates LGE images from $T_1$ maps rather than the acquiring LGE images directly. For example, synthetic LGE using post-contrast Modified Look-Locker inversion recovery (MOLLI) $T_1$ maps were shown to have comparable sensitivity and specificity to acquired LGE for scar detection. Further, synthetic LGE is time-efficient (as it only requires acquisition of a post-contrast $T_1$ map) and it has potential for reduced operator dependence, since optimal TI selection can be performed retrospectively without acquiring a separate TI scout. However, to date, synthetic LGE has only been used to generate bright-blood LGE images. Other contrast weightings, including dark-blood contrast, are more difficult to generate as they often require measurement of other tissue properties besides $T_1$.

A significant need exists for improved LGE MRI techniques for myocardium analysis to improve diagnostic accuracy and better inform treatment decisions.

SUMMARY OF THE INVENTION

In an aspect, a method for synthetic late gadolinium enhancement imaging includes: receiving, by one or more processors, magnetic resonance fingerprinting (MRF) image data of a subject from a scanning device and obtaining, from the MRF image data, a $T_1$ tissue property map and a $T_2$ tissue property map co-registered with the $T_1$ tissue property map; identifying, using the one or more processors, a plurality of regions of interest in the MRF image data, the plurality of regions of interest comprising at least one myocardium region and a blood region; determining, by the one or more processors, $T_1$ and $T_2$ values for each of the plurality of regions of interest; determining, by the one or more processors and based on the $T_1$ and $T_2$ values for the plurality of regions of interest, a plurality of different sets of pulse sequence parameters, each set of pulse sequence parameters being configured to correspond to a different image contrast condition; and generating, by the one or more processors, a different contrast image for each of the different sets of pulse sequence parameters, wherein at least one contrast image is a synthetic bright-blood LGE image and at least one contrast image is a synthetic dark-blood/gray-blood LGE image.

In another aspect, a non-transitory computer-readable storage medium storing executable instructions that, when executed by a processor, cause a computer to: receive magnetic resonance fingerprinting (MRF) image data of a subject from a scanning device and obtaining, from the MRF image data, a $T_1$ tissue property map and a $T_2$ tissue property map co-registered with the $T_1$ tissue property map; identify a plurality of regions of interest in the MRF image data, the plurality of regions of interest comprising at least one myocardium region and a blood region; determine $T_1$ and $T_2$ values for each of the plurality of regions of interest; determine, based on the $T_1$ and $T_2$ values for the plurality of regions of interest, a plurality of different sets of pulse sequence parameters, each set of pulse sequence parameters being configured to correspond to a different image contrast condition; and generate a different contrast image for each of the different sets of pulse sequence parameters, wherein at least one contrast image is a synthetic bright-blood LGE image and at least one contrast image is a synthetic dark-blood/gray-blood LGE image.

In yet another aspect, a computing system for magnetic resonance imaging (MRI) post late gadolinium enhancement (LGE) contrast includes: one or more processors; a tissue map analyzer application configured to be executed by the one or more processors: receive magnetic resonance fingerprinting (MRF) image data of a subject from a scanning device and obtain, from the MRF image data, a $T_1$ tissue property map and a $T_2$ tissue property map co-registered with the $T_1$ tissue property map; and identify a plurality of regions of interest in the MRF image data, the plurality of regions of interest comprising at least one myocardium region and a blood region; and a synthetic LGE image generator application configured to be executed by the one or more processors: determine $T_1$ and $T_2$ values for each of the plurality of regions of interest; determine, based on the $T_1$ and $T_2$ values for the plurality of regions of interest, a plurality of different sets of pulse sequence parameters, each set of pulse sequence parameters being configured to correspond to a different image contrast condition; and generate a different contrast image for each of the different sets of pulse sequence parameters, wherein at least one contrast image is a synthetic bright-blood LGE image and at least one contrast image is a synthetic dark-blood/gray-blood LGE image.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

This patent or application file contains at least one drawing executed in color. Copies of this patent or patent application publication with color drawing(s) will be provided by the United States Patent and Trademark Office upon request and payment of the necessary fee.

Figure 1:
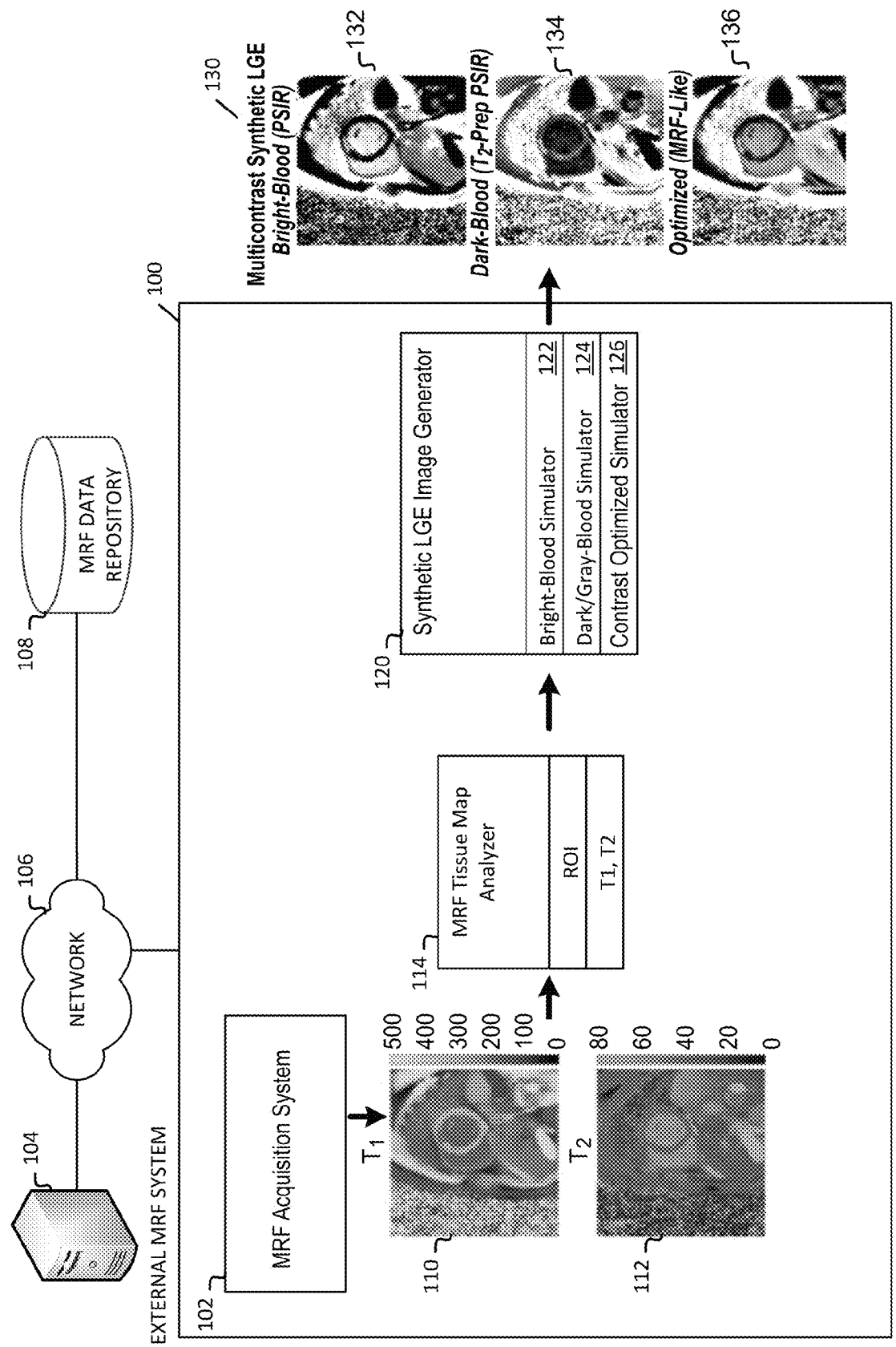

FIG. 1 illustrates an example schematic of a magnetic resonance fingerprinting (MRF) technique generating synthetic late gadolinium enhancement (LGE) images, in accordance with an example.

Figure 2:
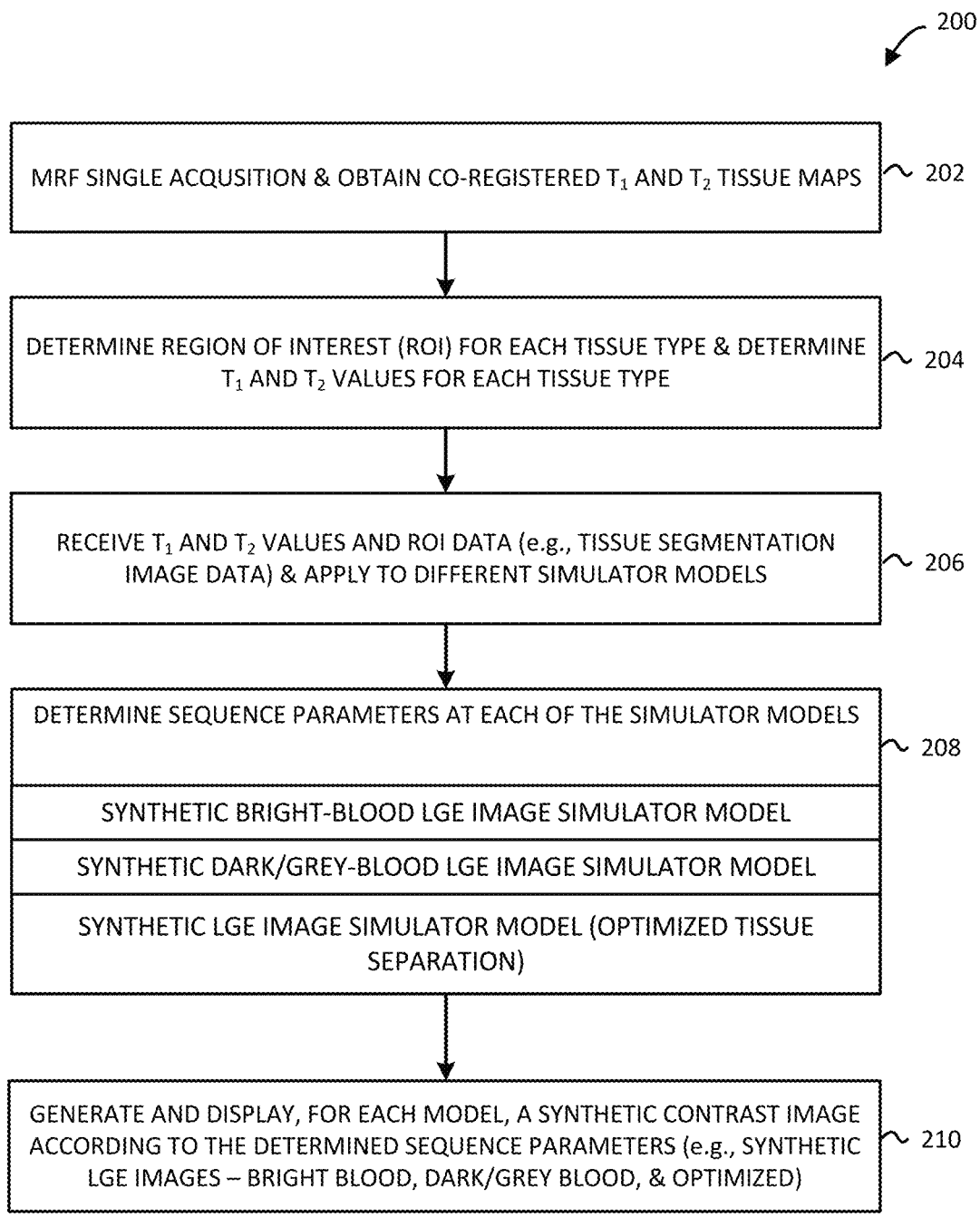

FIG. 2 illustrates an example process for generating synthetic LGE images using the MRF technique and schematic of FIG. 1, in accordance with an example.

Figure 3:
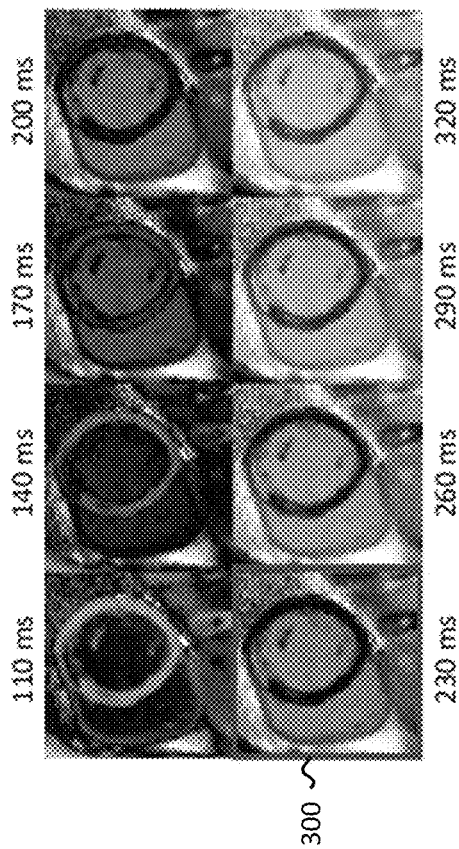

FIG. 3 illustrates synthetic bright-blood LGE images over a range of different inversion times, in accordance with an example.

Figure 4:
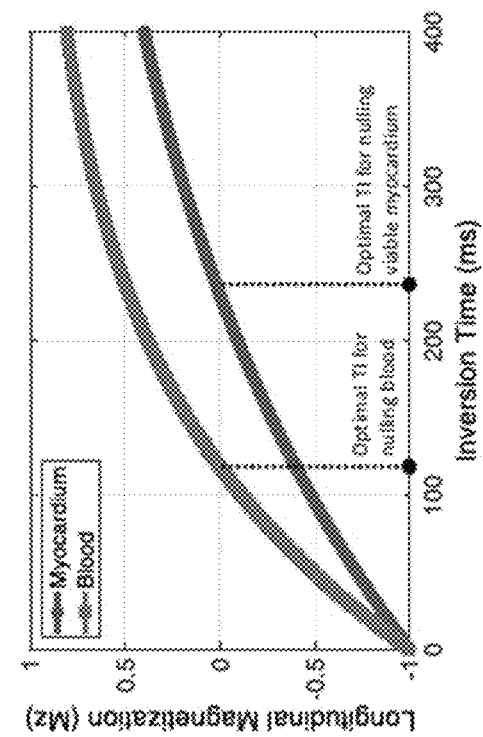

FIG. 4 is a plot of inversion time versus longitudinal magnetization, showing the inversion time that is automatically calculated to null signal from either blood or viable myocardium based on the post-contrast MRF $T_1$ maps, in accordance with an example.

Figure 5A:
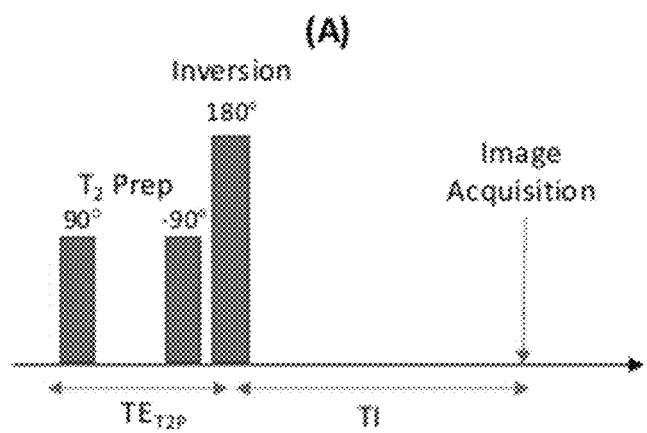
Figure 5B:
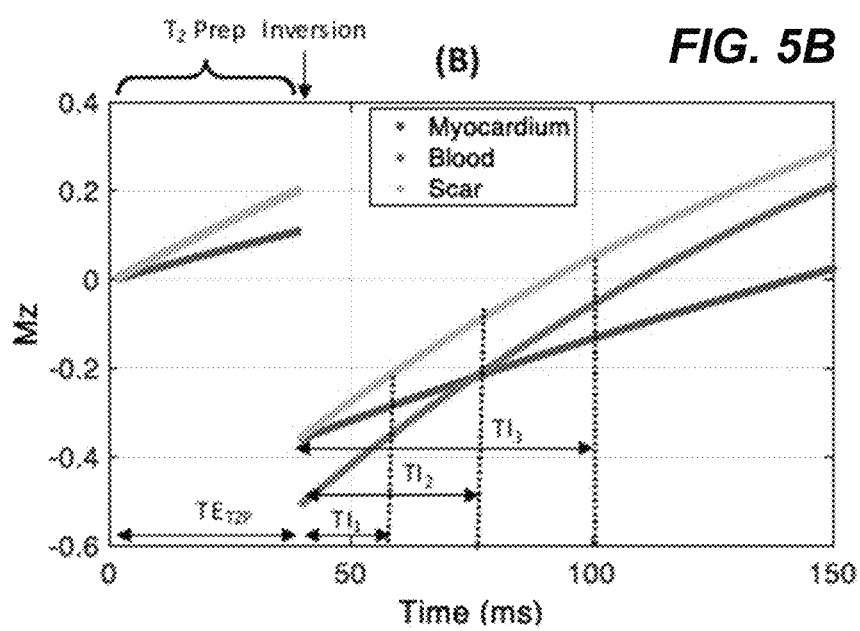

FIG. 5A illustrates a $T_2$-prepared inversion recovery MRI pulse sequence used to simulate the dark/gray-blood synthetic LGE images. FIG. 5B is a plot of the longitudinal magnetization over time for three different tissue types (myocardium, blood, and scar) using the pulse sequence of FIG. 5A; three time points are indicated on the plot corresponding to different degrees of blood signal suppression, in accordance with an example.

Figure 6:
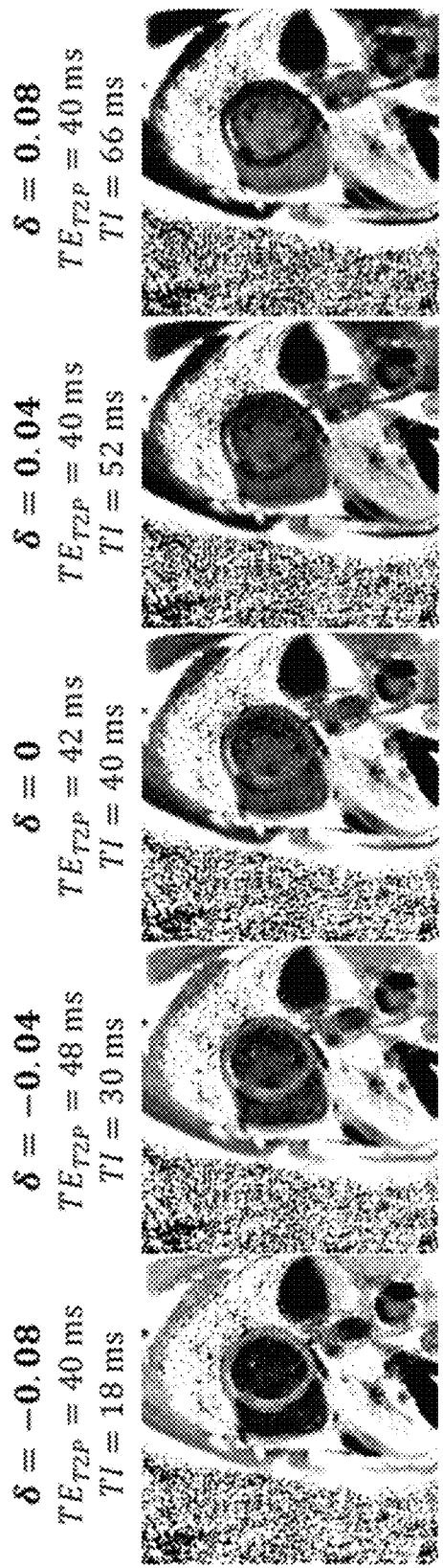

FIG. 6 illustrates images of generated synthetic dark-blood/gray-blood LGE images at different sequence parameter conditions, in accordance with an example.

Figures 7A, 7B, 7C:
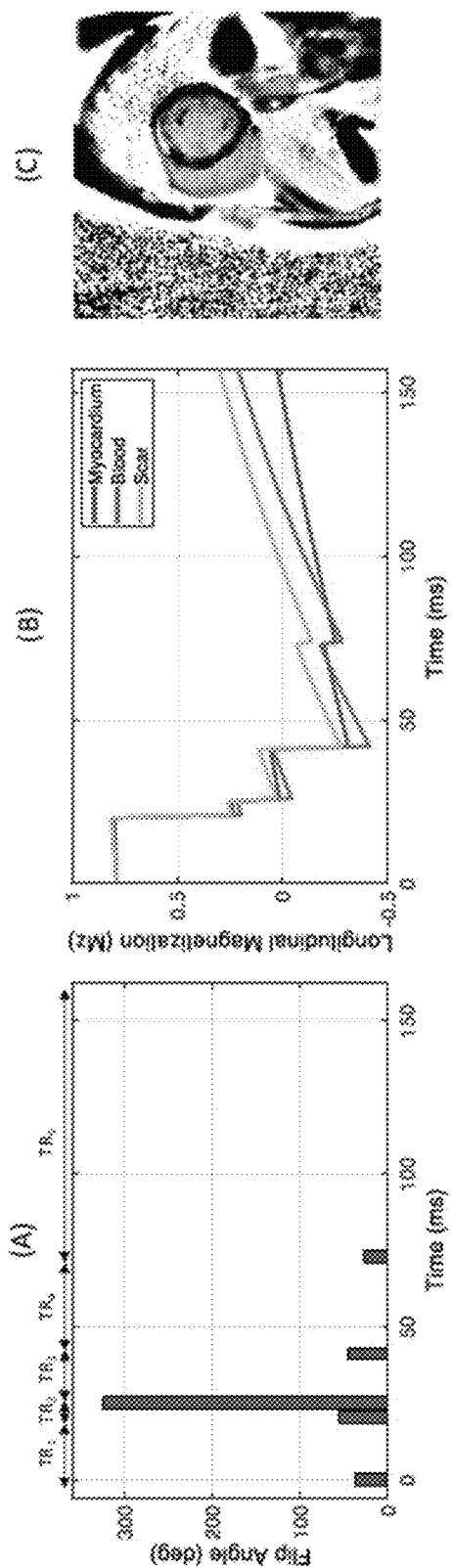

FIG. 7A is an example of an MRI pulse sequence used to simulate an "optimized contrast" synthetic LGE image, where the sequence parameters (e.g., flip angles and TRs) were numerically optimized to separate the signal intensities of blood, viable myocardium, and scar based on $T_1$ and $T_2$ values from MRF data. FIG. 7B is a plot of longitudinal magnetization versus time for the three different tissue types (myocardium, blood, and scar). FIG. 7C shows a synthetic LGE image using the optimized contrast technique, in accordance with an example.

Figure 8A:
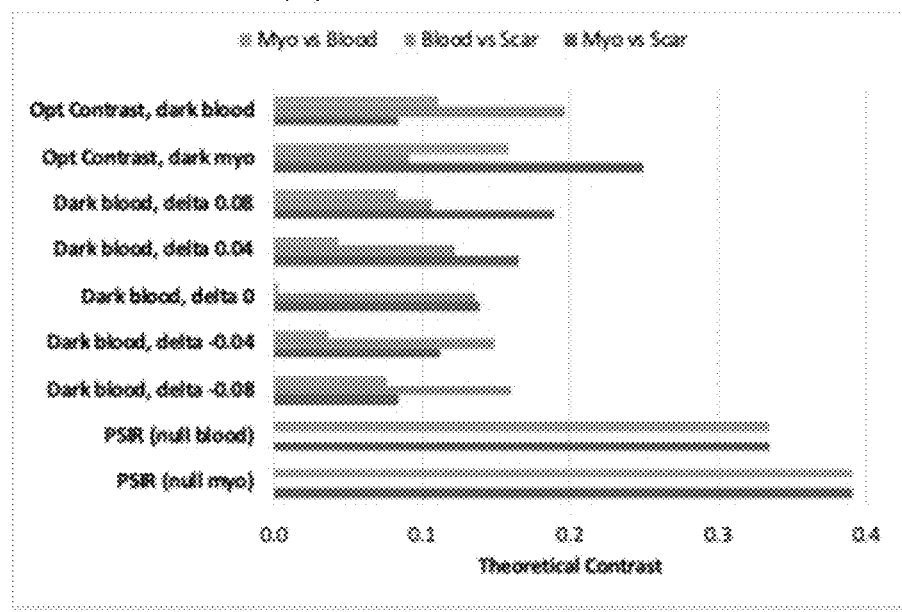
Figure 8B:
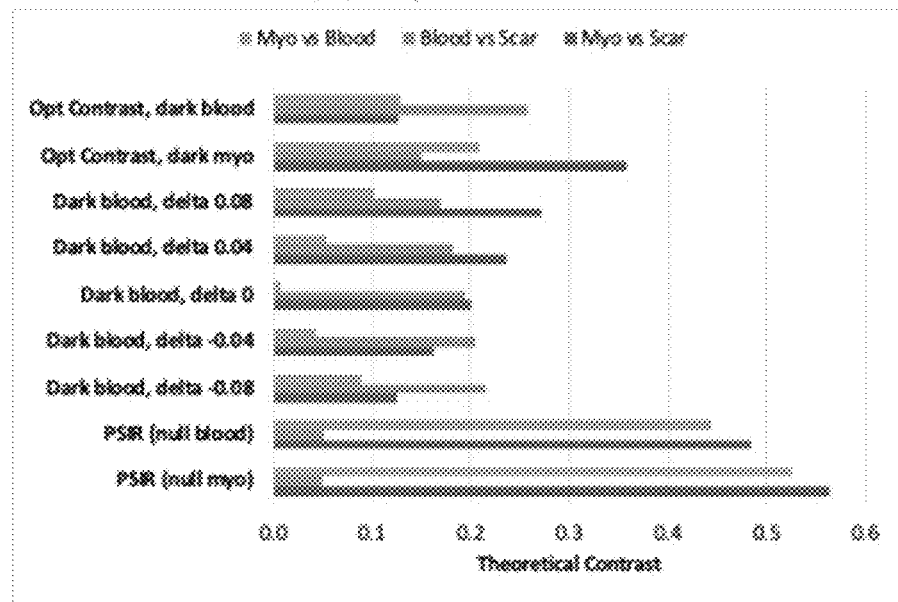

FIGS. 8A & 8B are plots of theoretical (i.e., based on Bloch equation simulations) and empirical (i.e., measured in patients) contrasts between different tissue types for MRF-derived synthetic LGE images with different types of contrast weightings, in accordance with an example.

Figure 9:
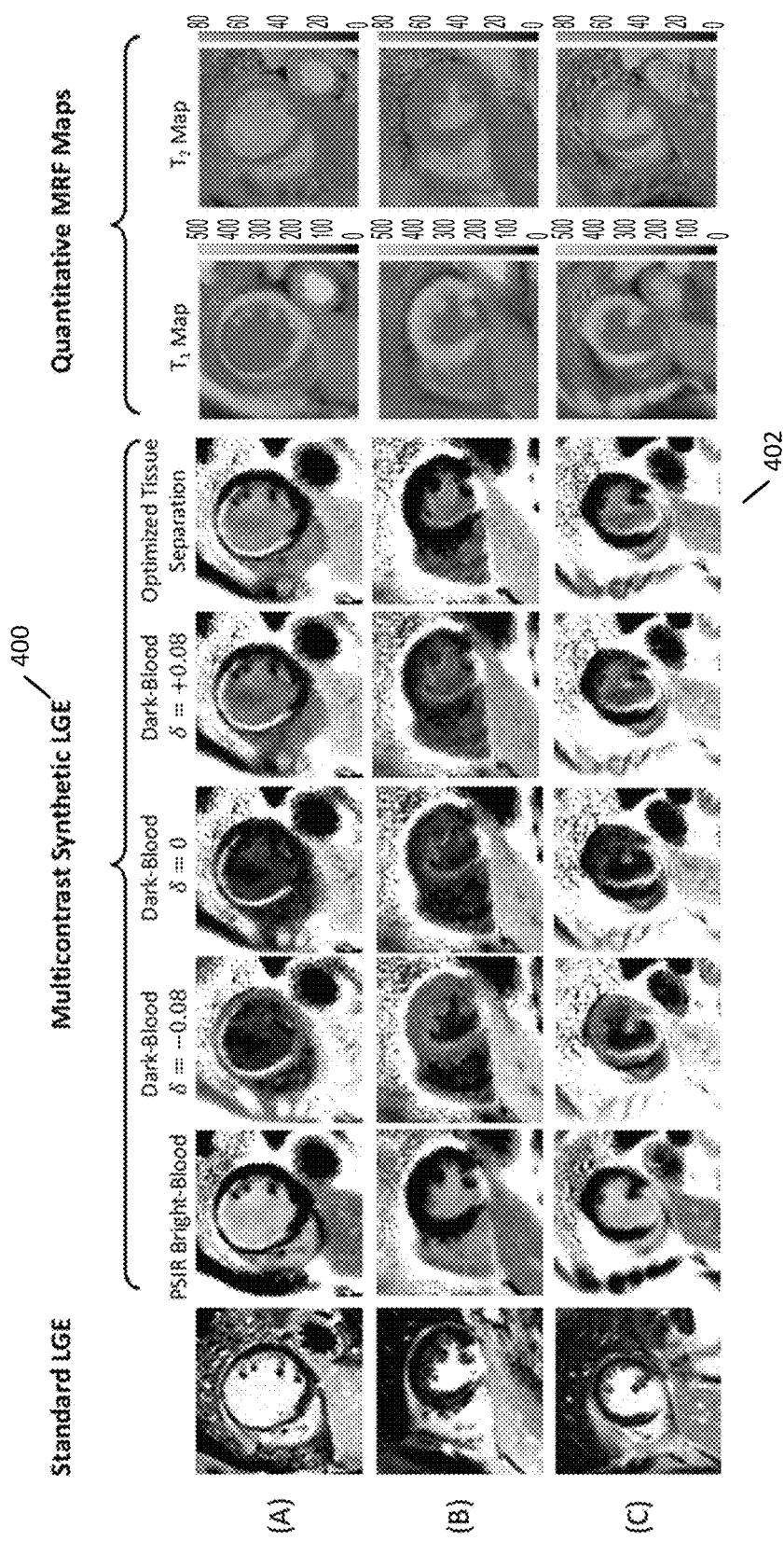

FIG. 9 illustrates multicontrast synthetic LGE images generated from post-contrast quantitative MRF tissue property maps using various techniques herein compared against conventional LGE imaging, for three different subjects (A, B, C), in accordance with an example.

Figure 10:
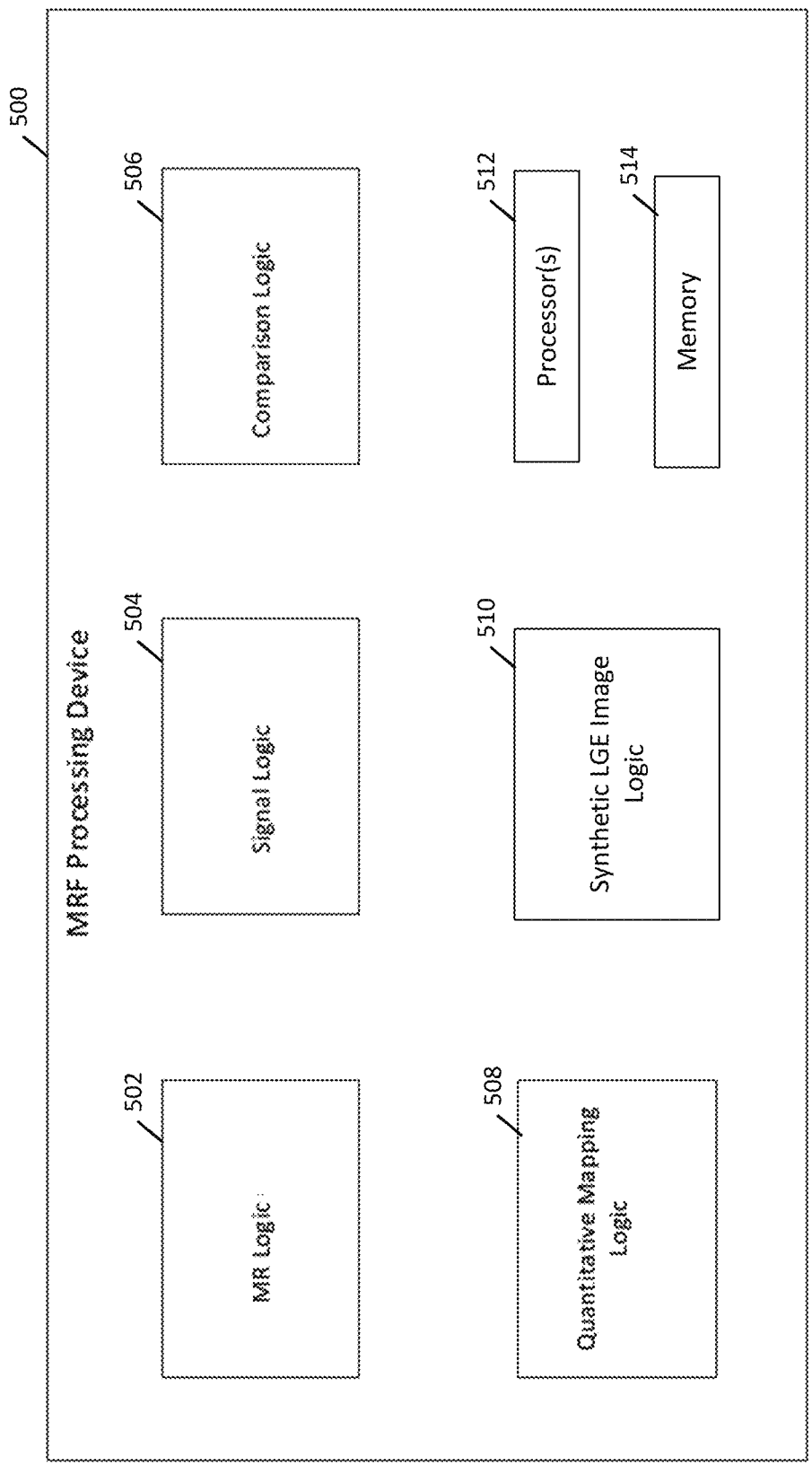

FIG. 10 illustrates an example MRF processing device in which the techniques of FIGS. 1-9 may be implemented.

Figure 11:
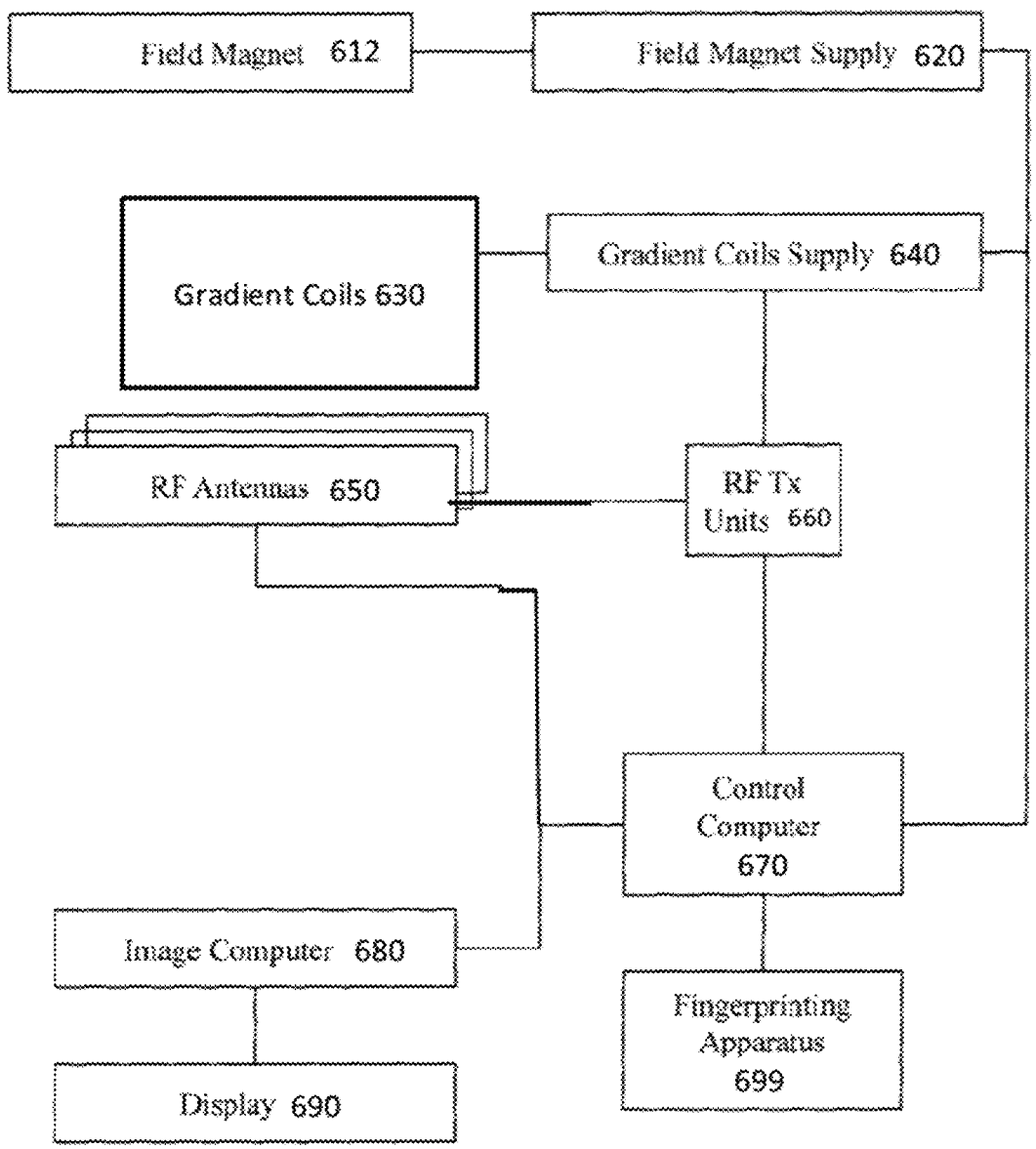

FIG. 11 illustrates an example MRF system which may include the MRF processing device of FIG. 10 and in which the techniques of FIGS. 1-9 may be implemented.

DETAILED DESCRIPTION

The present application includes methods and systems to generate late gadolinium enhancement (LGE) magnetic resonance images (MRI) using magnetic resonance fingerprinting (MRF). Magnetic resonance fingerprinting (MRF) is a quantitative framework for rapid and simultaneous parameter mapping that uses a time-varying magnetic resonance imaging (MRI) pulse sequence combined with dictionary-based pattern matching. While conventional LGE MRI is an entirely different technique, the present techniques include methods and systems that use MRF processes to generate synthetic LGE images for analysis, such as myocardial analysis. Advantageously, with the present techniques, synthetic LGE images may be generated using acquisition times that are much faster than that of conventional LGE MRI images, by exploiting the acquisition data obtained in a single MRF imaging acquisition. Instead of having to take different scans, at different times of a subject, to generate LGE images in conventional methods, MRF imaging allows for a single acquisition event, generating co-registered tissue maps (e.g., $T_1$ and $T_2$ maps) that may then be used for synthetic LGE image construction. These synthetic LGE images, once generated, may then be used to identify scar tissue, infarction, and diseases in cardiac tissue, with the same or greater levels of information accuracy as conventional LGE MRI techniques.

In various examples, the present techniques include methods and systems for performing MRF that are configured to use quantitative tissue property maps (e.g., $T_1$ and $T_2$ maps), which are acquired during a post-contrast MRF acquisition performed after administration of a gadolinium-based MRI contrast agent, to simulate LGE MRI pulse sequences. In particular, a single post-contrast MRF acquisition may be performed and, using the co-registered tissue property maps, different types of LGE MRI pulse sequences may be simulated where the scan parameters can flexibly adjusted in post-processing to enhance or suppress specific tissues, according to different sequence parameter rules, to generate synthetic LGE images. The result is that, in some examples, the present techniques are able to generate and display several LGE images with different contrast weightings simultaneously to a clinician for improved detection and delineation of tissue states within a subject, including importantly myocardial scar tissue and fibrosis, especially for subendocardial scar tissue. Further, with LGE images simulated from MRF obtained maps, the present techniques may avoid the need in conventional systems for dedicated LGE MRI pulse sequences to achieve each contrast weighting. Instead, with the present techniques, a more time-efficient process is achieved, where MRF may be used to acquire two-dimensional (2D) $T_1$ and $T_2$ maps during a relatively short breathhold (e.g., 15-heartbeat breathhold). Further, in various examples, the techniques herein include methods and systems configured to automatically select synthetic LGE scan parameters based on measured tissue map values (e.g. $T_1$ and $T_2$ values), where such automated parameter selection is able to simplify workflow, improve image quality, and improve reproducibility of LGE-based measurements by reducing operator dependence on image quality. In yet various other examples, the techniques herein are able to generate novel contrast weightings by optimizing arbitrary MRI pulse sequences to enhance or suppress specific tissues based on patient-specific tissue property maps (e.g., $T_1$ and $T_2$ maps) obtained using MRF.

FIG. 1 illustrates an example architecture of a system 100 for generating synthetic contrast images using MRF data, in accordance with the methods and processes described and illustrated herein. An MRF acquisition system 102 performs an acquisition on a subject, after administration of a gadolinium-based MRI contrast agent to the subject, e.g., an acquisition of a cardiac region of the subject. While the system 100 is illustrated as including the MRF acquisition system 102, in some examples, MRF data is obtained from an external MRF acquisition system 104 communicatively coupled to the system 100 through communication network 106. In some examples, the MRF data is stored in network accessible data storage, such as a cloud-based or cloud-accessible MRF data repository 108.

After performing the MRF acquisition itself or in response to otherwise receiving MRF data from an external source, the MRF acquisition system 102 identifies tissue maps from the acquired MRF data, which in the illustrated examples, results in a $T_1$ tissue map 110 and a $T_2$ tissue map 112. The $T_1$ and $T_2$ tissue maps 110/112 are provided to an MRF tissue map analyzer 114, which may be an application or any other series of computer-executable instructions, that analyzes the received tissue maps 110/112 and localizes image data in the maps through image segmentation or other processes and then determines $T_1$ and $T_2$ values in a region of interest (ROI) corresponding to those segmentations. For example, after the MRF acquisition of the $T_1$ and $T_2$ tissue maps 110/112, regions of interest (ROIs) may be manually identified by an operator by selecting regions in the tissue maps displayed on a monitor and using an input device. In particular, the operator may identify two or more regions of interest (ROIs), each containing a different tissue type. In the example of synthetic LGE image generation, those two or more different tissue types may be healthy (viable) myocardium and blood, resulting in a ROI for each. In other examples, the different tissue types identified within ROIs may be any combination of healthy myocardium, unhealthy (fibrosis, infarction or scarred) myocardium, blood, of any other tissue type of interest. In other examples, the MRF tissue map analyzer 114 automatically identifies ROIs in the tissue maps 110/112 for various tissue types (e.g. healthy myocardium, unhealthy (fibrosis, infarction or scarred) myocardium, and blood) using image pattern recognition processes, machine learning {discuss generally}, or other techniques. For example, the MRF tissue map analyzer 114 may be configured to automatically identify and segment viable myocardium and the left ventricular (LV) blood pool. Tissue map data corresponding to the ROI and to each of the different, identified tissue types may be stored as ROI data 116, as shown.

The MRF tissue map analyzer 114 is further designed to measure the $T_1$ and $T_2$ values for each different identified tissue type within the ROI data 116. For example, the mean $T_1$ and $T_2$ of each of healthy myocardium, unhealthy (fibrosis, infarction or scarred) myocardium, and blood may be determined from the tissue maps 110/112 and stored as data 118. In some examples, the MRF tissue map analyzer 114 identifies myocardial scar tissue. However, in some examples, such tissue may not be present or may be not visible in the tissue maps 110/112. As such, in some examples, the MRF tissue map analyzer 114 may include myocardial scar tissue model configured to approximate relaxation times of scar tissue. In an example, relaxation times for scar tissue are approximated by assuming the same $T_1$ as blood and the same $T_2$ as viable myocardium. This model is justified, in some examples, based on relaxation times measured using MRF in cardiomyopathy patients, the data shown in Table 1.

TABLE 1

| Tissue | $T_1$ (ms) | $T_2$ (ms) |
|---|---|---|
| Viable Myocardium | 295 +/− 35 | 37 +/− 6 |
| LV Blood | 187 +/− 32 | 66 +/− 7 |
| Myocardial Scar | 187 +/− 26 | 40 +/− 7 |

The ROI data 116 and $T_1$ and $T_2$ data 118 are provided to a synthetic LGE image generator 120, which may be an application or any other series of computer-executable instructions, that performs a number of processes, including MRI pulse sequence simulation to generate multicontrast synthetic LGE images 130. In some examples, the synthetic LGE image generator 120 includes different MRI pulse sequence models constructed from tissue property maps, in particular tissue properties determined from MRF tissue maps, such as one or more of $T_1$ and $T_2$. For the system 100 to generate synthetic LGE images, in an example, the synthetic LGE image generator 120 includes three different simulators of MRI pulse sequences for generating bright-blood images (a simulator 122), a dark/gray blood images (a simulator 124), and optimized contrast images (a simulator 126), examples of which are discussed in further detail in reference to FIG. 2. The pulse sequence simulators 124-126 may be constructed from any of a number of different pulse sequence parameters—including for example, inversion times, $T_2$ preparation times, flip angles, repetition times, echo times, radiofrequency (RF) phase—as well as tissue property values—for example, $T_1$ and $T_2$ values. For each example simulator 122-126, the synthetic LGE image generator 120 is designed to automatically determine the sequence parameter values that will be used to generate respective synthetic images. The sequence parameter values and, in some examples, the ROI data 116 and/or $T_1$/$T_2$ data 118, are provided to the pulse sequence simulators and the synthetic LGE image generator 120 generates different synthetic LGE images 130. In the illustrated example, synthetic LGE image generator 120 generates a different contrast image 132, 134, and 136, for each different simulator 122, 124, and 126.

An example process 200 that may be implemented by the system 100 to generate the synthetic LGE images 132, 134, and 136 is shown in FIG. 2. Initially, MRF data are acquired in a single acquisition post-contrast application, for example, in a single 15-heartbeat breathhold (process 202), and co-registered $T_1$ and $T_2$ tissue maps are obtained. At a process 204, the $T_1$ and $T_2$ tissue maps are provided to a tissue map analyzer that determines regions of interest for each of a plurality of different tissue types to determine $T_1$ and $T_2$ values for each tissue type—for example, by measuring the mean $T_1$ or $T_2$ value of all pixels within the ROI for a specific tissue. The plurality of regions of interest may be segmented from one another in the tissue map image data in forming the ROI image data. In addition to the ROI image data, the process 206 receives the computed $T_1$ and $T_2$ values from the MRF acquisition, which are used to determine the different sequence parameters, per simulator models. In an example, the process 206 applies this input data to three different sequence parameter simulators each applying a model (containing a set of assumptions, rules, and/or processes for determining sequence parameters) to generate synthetic LGE images with various contrast weightings obtained by simulating different MRI pulse sequences. A process 208 then determines sequence parameters, from this input data, and specifically sequence parameters corresponding to different simulator models designed for LGE image simulation. For example, at the process 208, sequence parameters (e.g., inversion times, etc.) may be automatically calculated based on the measured $T_1$ and $T_2$ values for viable myocardium, blood, and myocardial scar using different models in the process 206. In the illustrated, the process 208 includes the three simulator models: a synthetic bright-blood LGE image simulator model that uses $T_1$ map to simulate a phase sensitive inversion recovery (PSIR) sequence; a synthetic dark/gray-blood LGE image simulator model that uses both $T_1$ and $T_2$ maps to simulate a $T_2$-prepared PSIR sequence; and a synthetic LGE image simulator model that performs an optimized tissue separation contrast, e.g., using an MRF-like sequence of arbitrary RF pulses and timings optimized to distinguish among scar/fibrosis, blood, and viable myocardium. The process 208 determines sequence parameters for each of the simulator models and, at a process 210, these sequence parameters are used by the synthetic LGE image generator 120 to generate the synthetic contrast images.

Example implementations of various sequence parameter simulator models, including that of process 208, will now be described.

Example Synthetic Bright-Blood PSIR LGE Image

In an example, the synthetic LGE image generator 120 includes the bright-blood simulator 122 used at the process 208 to generate corresponding sequence parameters from which MRI pulse sequences are determined to generate a synthetic bright-blood LGE image. In an example of the simulator 122, a bright-blood phase sensitive inversion recovery (PSIR) LGE image is simulated using the post-contrast $T_1$ map according to the following model:

$$S_{PSIR} = 1 - 2e^{-\frac{TI}{T_1}} \quad \text{(Eq. 1)}$$

where TI is the inversion time. A magnitude image is obtained according to:

$$S_{MAG} = |S_{PSIR}| \quad \text{(Eq. 2)}$$

Because the LGE images are simulated rather than acquired, at the process 208, images at multiple TIs can be reconstructed by LGE sequence parameter modeler 120 to retrospectively identify the TI that best nulls signal from viable myocardium without requiring a TI scout scan. Example synthetic PSIR images at different inversion times obtained by using a post-contrast MRF $T_1$ map in Eq. 1 are shown in FIG. 3, where in this example an optimal image 300 at which the TI best null signals the viable myocardium corresponds to an inversion time of 230 ms. To reduce operator dependence, the LGE sequence parameter modeler 120 may be configured to automatically determine the TI needed to null a specific tissue using Eq. 1 based on the tissue's $T_1$ measurement from the MRF scan. For example, the model may include instructions to substitute the measured MRF $T_1$ value for viable myocardium into Eq. 1 and determine the TI needed to null viable myocardium (i.e., by setting $S_{PSIR}$ equal to zero and solving for the TI). Using this TI value, a synthetic PSIR image is generated by using Eq. 1 to calculate the signal ($S_{PSIR}$) at every pixel using the post-contrast MRF $T_1$ map. A synthetic magnitude inversion recovery image can be obtained using Eq. 2 (i.e., by taking the absolute value of the synthetic PSIR image). While viable myocardium is traditionally the tissue that is nulled in conventional LGE scans, a synthetic PSIR image could also be generated using Eq. 1 where the TI is chosen to null signal from a different tissue type (e.g., blood) using the same procedure, if desired. FIG. 4 illustrates an example determination of an optimum TI value, i.e., that results in signal nulling. In some examples of the process 208, longitudinal magnetization values may be plotted (or otherwise examined) as a function of inversion time for a specific tissue type (e.g., viable myocardium) and an optimal TI for signal nulling may be used and, in this way, the MRI pulse sequence parameter (e.g., TI) value is determined.

Example Synthetic Dark/Gray-Blood PSIR LGE Image Using $T_2$-Prepared Inversion Recovery In an example, the synthetic LGE image generator 120 includes the dark/gray-blood simulator 124 used at the process 208 to generate corresponding sequence parameters from which MRI pulse sequences are determined to generate a synthetic dark/gray-blood LGE image.

Subendocardial scar can be difficult to distinguish on conventional PSIR LGE images due to the similar post-contrast $T_1$ values of blood and scar. The simulator 124, however, is configured with a model based off $T_2$-prepared inversion recovery LGE which leverages the short $T_2$ of scar and long $T_2$ of blood to differentiate these tissues despite their similar $T_1$ values (e.g., Table 1). The model includes adjustable sequence parameters, in particular, the $T_2$ prep duration ($TE_{T2P}$) and inversion time (TI). FIG. 5A illustrates a $T_2$-prepared inversion sequence, in an example. With proper selection of these sequence parameters, by the simulator 124, signal from blood and signal from viable myocardium are suppressed while maintaining high signal from scar tissue. Using this sequence, the process 208, e.g., the simulator applying its simulator model, can completely suppress blood so that it appears black and partially suppress viable myocardium so it appears gray, or vice versa, which is important for delineating the myocardial wall to evaluate scar transmurality. FIG. 5B illustrates longitudinal magnetization values for different inversion times. As illustrated, the process 208 may determine an inversion time sequence parameter to achieve any number of different degrees of blood suppression from the plotted data. The signal from blood is lower than the viable myocardium at TI1; The signal from blood and from myocardium are equally suppressed at TI2; and the signal from myocardium is lower than blood at TI3.

In an example implementation, the synthetic dark-blood PSIR LGE image model is executed by performing a Bloch equation simulation for a $T_2$-prepared inversion recovery scan using MRF $T_1$ and $T_2$ maps. While dark-blood LGE images could be reconstructed over a range of TI and $TE_{T2P}$ values to visually select the desired image contrast, allowing an operator to manually adjust sequence parameters, in an example, the process 208 executes an automated method to choose the pulse sequence parameter values. In an example, we defined a parameter δ that controls the suppression of blood and viable myocardium signals. Setting δ=0 causes viable myocardium and blood to have the same signal intensity so both are equally suppressed. Setting δ>0 causes blood to have a higher signal than viable myocardium so the former appears gray while the latter appears black when windowed appropriately (referred to here as a "gray-blood" image). Setting δ<0 causes blood to have a lower signal intensity than viable myocardium, so blood appears black and viable myocardium appears gray when appropriately windowed (referred to here as a "dark-blood" image). The steps in an example dark-blood/gray-blood LGE sequence parameter determination are given by the below model:

Step 1: Select a value for δ, where δ is a parameter determining a level of blood signal suppression compared to viable myocardium, with δ<0 resulting in blood having a lower signal intensity than viable myocardium and δ>0 resulting in the blood having a higher signal intensity than viable myocardium.

Step 2: Using the $T_1$ and $T_2$ values determined for viable myocardium, blood, and unhealthy (fibrosis, infarcted, or scarred) myocardium from the MRF scan, determine the TI and $TE_{T2P}$ that satisfy the following optimization problem:

$$\max_{TI, TE_{T2P}} |M_z^{myo} - M_z^{scar}| + |M_z^{blood} - M_z^{scar}| \quad (Eq. 3)$$

$$s.t. M_z^{blood} - M_z^{myo} - \delta < 0 \quad (Eq. 4)$$

where the longitudinal magnetization for viable myocardium, blood, and unhealthy (fibrosis, infarcted, or scarred) myocardium are denoted by $M_z^{myo}$, $m_z^{blood}$, and $m_z^{scar}$, respectively.

Step 3: For every pixel in the MRF $T_1$ and $T_2$ maps, perform a Bloch equation simulation of a $T_2$-prepared inversion recovery sequence using the TI and $TE_{T2P}$ calculated in Step 2. The output of the Bloch equation simulation is the synthetic LGE image with dark-blood or gray-blood contrast (depending on the choice of δ).

This automated parameter value selection (Steps 1-3), in an example, took approximately 60 ms and the image simulation (Step 5) took 90 ms running on a single CPU in MATLAB. FIG. 6 shows examples of generated synthetic dark-blood/gray-blood LGE images calculated for different values of the sequence parameter δ using the proposed model. As noted, in some implementations, the user may be allowed to dynamically adjust the parameter δ to flexibly display synthetic LGE images with different levels of blood signal suppression (i.e., dark-blood and gray-blood contrast weightings).

Example Synthetic LGE Image with Optimized Tissue Separation

In an example, the synthetic LGE image generator 120 includes the contrast optimized simulator 126 used at the process 208 to generate corresponding sequence parameters from which MRI pulse sequences are determined to generate a synthetic LGE image that maximizes the separation among several tissues of interest, such as viable myocardium, blood, and unhealthy (scarred, infarcted, or fibrotic) myocardium. That is, in addition to simulating conventional pulse sequences like inversion recovery, the system 100 determines synthetic LGE images by simulating an MRF-like sequence with variable flip angles and repetition times, which are optimized to enhance differences in signal intensities among the tissues of interest (i.e., viable myocardium, blood, and unhealthy myocardium). In an example, the simulator model is configured based on the hypothesis that the larger degrees of freedom in the pulse sequence will lead to better separation of signals from different tissues, which will ultimately improve the delineation of scar and fibrosis. The process is a contrast weighting process for optimal tissue separation. In an example, the process 208 determines a variable-length sequence of flip angles, RF phases, and TRs that maximally separate longitudinal magnetization values between different tissue types. The process 208 then generates the synthetic LGE image by performing a Bloch equation simulation on the flip angles, RF phases, and TRs and on the $T_1$ and $T_2$ values for the different tissue types.

In an example, the steps in generating the resulting synthetic images, in an example, are provided by the below model:

Step 1: Select a value for n, the number of RF pulses in the sequence (e.g., we used n=5 in some examples, see, e.g., FIG. 7A).

Step 2: Randomly initialize a sequence of n flip angles (α) between 0-360°, RF phases (ψ) between 0-360°, and repetition times (TR) between 0-500 ms. These sequence parameters may be collectively denoted θ={$α_1$, $ψ_1$, $TR_1$, $α_2$, $ψ_2$, $TR_2$, ..., $a_n$, $ψ_n$, $TR_n$}, where TR is repetition time and α is the flip angle.

Step 3: A numerical optimization is performed. On each iteration, the flip angles and TRs are updated to minimize a cost function $f(θ)$. Although many cost functions may be used in the model, for the illustrated example, the model used the following cost function executed by the process 208:

$$f(\theta) = \frac{\lambda_1}{|M_z^{scar}(n) - M_z^{blood}(n)|} + \frac{\lambda_2}{|M_z^{scar}(n) - M_z^{myo}(n)|} + \frac{\lambda_3}{|M_z^{myo}(n) - M_z^{blood}(n)|} \quad (Eq. 5)$$

$$\min_\theta f(\theta) \text{ s.t. } M_z^{myo} \leq M_z^{blood} \leq M_z^{scar} \quad (Eq. 6)$$

This cost function penalizes sequences if the signal intensities of any tissues are too similar. The coefficients $λ_1$, $λ_2$, and $λ_3$ can be tuned, although we set them to 1 to give equal weighting to all terms (see, FIG. 7B). The inequality constraint (Eq. 6) specifies that the order of tissues from highest to lowest signal intensity should be scar, blood, and viable myocardium (so these tissues appear white, gray, and black when the image is windowed appropriately), although this order can be changed.

FIGS. 7A-7C illustrate an example of generation of a synthetic LGE image with optimized tissue separation calculated for n=5 RF pulses, as would be performed by system 100 according to processes 208-212. FIG. 7A is an example from one patient, where the present techniques output different optimized pulse sequences depending on the patient's specific $T_1$ and $T_2$ values. For the illustrated example, the optimization was performed in MATLAB using fmincon and was repeated 200 times with random initial sequences. Out of the 200 solutions, the sequence that minimized cost function (Eq. 5 and 6) was used to simulate the final image. The entire optimization took approximately 10 s running on 12 parallel CPUs.

EXAMPLE EXPERIMENT

Seven patients with ischemic cardiomyopathy were scanned on a 1.5 T MRI scanner in an IRB-approved, HIPAA-compliant study. Standard bright-blood LGE imaging over a 2D short-axis stack of the left ventricle was performed 10 minutes post-injection with an inversion recovery balanced steady-state free precession (IR-bSSFP) sequence with the following typical parameters: field-of-view (FOV) 360×200 mm$^2$, slice thickness 8 mm, acquisition matrix 256×144, in-plane resolution 1.4×1.4 mm$^2$, TR/TE 2.4/1.2 ms, flip angle 45°, bandwidth 780 Hz/pixel. The TI was selected manually after a scout scan. Post-contrast 2D cardiac MRF scans were also acquired at apical, medial, and basal slices with the following parameters: FOV 300×300 mm$^2$, slice thickness 8 mm, acquisition matrix 192×192, in-plane resolution 1.6×1.6 mm$^2$, TR/TE 5.4/1.4 ms, flip angles 4-25°, 15-heartbeat breathhold per slice, 254 ms diastolic acquisition window, 720 total TRs. For each MRF acquisition, a dictionary with 7292 entries was simulated with $T_1$[50:5:500 510:10:1000]ms and $T_2$[6:2:80 85:5:120 130:10:200]ms. The dictionary is scan-specific and includes the heart rate timings obtained from the ECG. The dictionary is compressed along the time dimension from 720 TRs to a low-dimensional subspace with rank 4, which retains 99.9% of the total energy of the uncompressed dictionary. MRF images in the temporal subspace are reconstructed using an iterative low-rank method with locally low-rank regularization (6×6 patch size) and matched to the dictionary to obtain co-registered $T_1$ and $T_2$ maps.

EXPERIMENTAL RESULTS

The contrast between viable myocardium, blood, and scar in the multicontrast synthetic LGE images was calculated for all seven patients. The following synthetic images were compared: 1) PSIR with nulling of viable myocardium and with nulling of blood; 2) $T_2$-prepared PSIR with δ=−0.08, −0.04, 0, 0.04, and 0.08; 3) optimized tissue separation with dark viable myocardium, gray blood, and bright scar; 4) optimized tissue separation with dark blood, gray viable myocardium, and bright scar. The theoretical contrast between two tissues A and B was calculated based on the simulated longitudinal magnetization as $|M_Z^B - M_Z^A|$. The empirical contrast was calculated as $|S^B - S^A|$, where $S^A$ and $S^B$ are the average signal within ROIs drawn in tissues A and B on the synthetic image.

Results averaged over all patients are shown in FIG. 8B compared to theoretical results in FIG. 8A. The PSIR bright-blood images have the highest contrast between viable myocardium and scar but poor contrast between blood and scar. The T2-prepared dark-blood images (at various δ values) have lower contrast between viable myocardium and scar compared to bright-blood images, but blood/scar contrast is improved. There is a tradeoff in the dark-blood imaging between blood/scar and myocardium/scar contrast; as δ (which controls the level of blood suppression) is increased from −0.08 to +0.08, the blood/scar contrast decreases while the myocardium/scar increases. The optimized tissue separation images achieve a good balance between the PSIR bright-blood and $T_2$-prepared dark-blood sequences; the contrast between blood/scar is higher compared to PSIR bright-blood (although lower than $T_2$-prepared dark-blood), and the contrast between myocardium/scar and myocardium/blood is higher compared to $T_2$-prepared dark-blood (although still lower than PSIR bright-blood). Of the optimal tissue separation images, the dark myocardium/gray blood image has better contrast between myocardium and scar but lower contrast between blood and scar compared to the gray myocardium/dark blood image.

Examples in Ischemic Cardiomyopathy Patients

FIG. 9 shows examples of multicontrast synthetic LGE images 400 generated with the present techniques in three representative patients (A, B, C) with ischemic cardiomyopathy, along with the post-contrast MRF $T_1$ and $T_2$ maps used to generate the synthetic images and acquired (reference) bright-blood PSIR LGE images. The Patient A has subendocardial scar, which is more clearly delineated on the synthetic dark-blood and synthetic optimized tissue separation LGE compared to the bright-blood LGE images (both acquired and synthetic). Focal inferior scar is visible on all synthetic and acquired images for Patient B. Focal inferior scar is also visible in the images for Patient C. The synthetic LGE image generated by numerically optimizing the contrast between different tissue types from among different tissue regions of interest is in column 402 (also termed "optimized tissue separation").

The present techniques thus provide methods and systems for generating synthetic multicontrast LGE images from post-contrast MRF $T_1$ and $T_2$ maps. The techniques are time efficient since LGE images with multiple $T_1$ and $T_2$ weightings can be calculated from a single MRF acquisition, which is collected during one breathhold. The synthetic images generated with the present techniques may be used in known downstream image processing, including (but not limited to): identification of myocardial segments with scar, classification of abnormal LGE signal intensity as ischemic or nonischemic in origin, measurement of scar area, and measurement of scar transmurality, which is a surrogate of myocardial viability. Additionally, synthetic LGE imaging may facilitate identification of diseases characterized by myocardial inflammation (e.g. myocarditis or sarcoid) or infiltration (e.g. cardiac amyloid). The present techniques may enable more accurate and reproducible diagnosis of both ischemic and nonischemic cardiomyopathies.

Referring next to FIG. 10, MRF processing device 500 is a processing device for analyzing MR images, and includes one or more logic modules 502, 504, 506, 508, and/or 510, and that represents an implementation of the MRF acquisition system 102. Depending on the implementation, the logic modules 502, 504, 506, 508, and/or 510 may be implemented in the MRF processing device 500 as hardware, software, firmware, or some combination of such. MRF processing device 500 simultaneously quantifies MR parameters including $T_1$, $T_2$, and proton density for an object to which the MRF processing device 500 applies an MRF pulse sequence. In one embodiment, MRF processing device 500 provides an MR image that facilitates identifying certain tissues based on their relative hypo-intense or hyper-intense appearance on an MR image (e.g., $T_1$ weighted image, $T_2$ weighted image).

MRF processing device 500 includes an MR logic module 502. The MR logic module 502 repetitively and variably samples an object in a (k, t, E) space to acquire a set of MR signals that may have non-constant amplitude and/or phase. For the (k, t, E) space, the k may be a point in k-space representing a spatial frequency of an MR image. In some implementations, the MR logic 502 may determine the value of k based on a Fourier Transform (FT) of the MR image. The t in the (k, t, E) space represents time, and the E represents one or more MR parameters for the MR image in question. Members of the set of MR signals are associated with different points in the (k, t, E) space. In different examples, the different points are sampled according to a plan where t and/or E varies non-linearly and/or in a non-constant manner.

The MR logic module 502 may sample the object using a diffusion-weighted double-echo pulse sequence. In some examples, the MR logic module 502 may employ a spiral readout. The pulse sequence may produce multiple signals per cycle of repetition time (TR). For example, both a free induction decay (FID) signal and an echo signal may be produced per TR. In some implementations, the FID signal is acquired using a variable density spiral-out trajectory and the spin echo signal is acquired using a variable density spiral-in trajectory. In further implementations, one signal may be more attuned with either of the $T_1$ tissue map or the $T_2$ tissue map. For example, the FID signal may be more $T_1$-weighted and the echo signal may be more $T_2$-weighted. In still further implementations, the MR logic module 502 may insert a mono-polar diffusion gradient between the FID and the spin echo. Inserting the mono-polar diffusion gradient may increase the diffusion sensitivity of the pulse sequence. In some examples, the MR logic module 502 may acquire the FID and the spin echo with varying flip angles, varying repetition times, and varying diffusion gradient moments.

In some examples, MRF processing device 500 also includes a signal logic module 504. Signal logic module 504 produces an MR signal evolution from the acquired MR signals. The signal evolution may include a number of MR signals acquired over a period of time. The set of MR signals may include transient-state signals associated with the MRF pulse sequence, a free induction decay signal, and a spin echo signal.

In further examples, MRF processing device 500 also includes a comparison logic module 506. The comparison logic module 506 compares reference information with at least one of the produced MR signal evolution or information associated with the produced MR signal evolution. In some implementations, the comparison logic module 506 determines whether a match exists between signals included in the reference information and at least one of the produced MR signal evolution or information associated with the produced MR signal evolution based on whether the comparison logic module 506 determines there to be an exact match. In other implementations, an exact match is not necessary, and the comparison logic module 506 may determine that there exists a match where signals are similar. Depending on the implementation, a match may be the signal that most closely matches another signal and/or the first signal that matches another signal to within a threshold. A match may be found by template matching, pattern matching, or other comparison approaches. The reference information may be, for example, a previously acquired signal evolution, a simulated signal evolution, an item derived from a signal evolution other than the produced MR signal evolution, and/or any other similar information. The reference information may include signal evolutions from different tissue types (e.g., healthy, diseased, advanced disease, etc.).

In still further examples, MRF processing device 500 also includes a quantitative mapping logic module 508. Quantitative mapping logic module 508 simultaneously produces quantitative maps for $T_1$, $T_2$, proton density, and diffusion associated with the object being scanned, based at least in part on the stored signal evolution that matches the MR signal evolution. The MR parameters may be retrieved from a data store that links stored MR parameters to the reference information. Quantitative mapping logic module 508 may also display the quantitative maps or cause the quantitative maps to be displayed.

While comparison logic module 506 and quantitative logic module 508 are illustrated as being part of MRF processing device 500, in some examples, the comparison logic module 506 and quantitative mapping logic module 508 may reside in an apparatus separate from the MRF processing device 500. In such examples, MRF processing device 500 may provide MR signals to the separate apparatus housing comparison logic module 506 or quantitative mapping logic module 508. In further examples, comparison logic module 506 and/or quantitative mapping logic module 508 may reside in separate apparatuses.

In still further examples, MRF processing device 500 also includes a synthetic LGE image logic module 510 for implementing the techniques herein, including those described in reference to MRF tissue map analyzer 114 and synthetic LGE image generator 120 of FIG. 1 as well as the method and processes described in reference to FIGS. 1-9.

While shown as separate logic modules 502-510, each of which may be implemented in hardware having one or more processors and memory, in some examples, the MRF processing device 500 is implemented having one or more processors 512 that may implement the operation of the logic modules 502-510. Further the processing device 500 may have a computer-readable memory 514 having instructions that may be executed by the one or more processors 512 and/or logic modules 502-510 to perform the methods and processes described herein, such as those in reference to FIGS. 1-9

Referring next to FIG. 11, MRF system 600 is an example MR system configured with a fingerprinting apparatus 699 to facilitate MR fingerprinting, and as may be implemented as the MRF acquisition system 102. Depending on the implementation, the fingerprinting apparatus 699 is and/or includes elements of MRF processing device 500 as described with regard to FIG. 10 above. In further implementations, the fingerprinting apparatus 699 performs example methods such as example method 200 as described above. While fingerprinting apparatus 699 is illustrated as part of MRF system 600 in one example, fingerprinting apparatus 699 may be a separate apparatus or apparatuses.

The system 600 includes one or more field magnets 610 and a field magnet supply 620. In some implementations, the field magnets 610 produce a uniform $B_0$ field—i.e. the main static magnetic field of the MRF system 600. However, in other implementations, the $B_0$ field is not uniform. In such implementations, the magnetic field instead varies over an object that the MRF system 600 analyzes. MRF system 600 further includes gradient coils 630 configured to emit gradient magnetic fields. The gradient coils 630 may be controlled, at least in part, by a gradient coil supply 640. In some implementations, the timing, strength, and orientation of the gradient magnetic fields may be controlled, and thus selectively adapted, during an MR procedure. As described above, the gradient coils 630 may commonly correlate signals with each other. As such, in some implementations, the system 600 may mistake noise from multiple coils as being an actual signal, resulting in skewed denoising. In such implementations, to counter such correlation, the system 600 performs a decorrelation procedure before performing the techniques described in FIGS. 1-9. The decorrelation procedure may be a pre-whitening procedure, an extraction procedure, or any other similar procedure as known in the art.

In some implementations, MRF system 600 includes a set of RF antennas 650 that generate RF pulses and receive resulting MR signals from an object that the MRF system 600 scans—i.e. the object to which the RF antennas 650 direct the RF pulses. In further implementations, the MRF system 600 controls how the pulses are generated and how the resulting MR signals are received. As such, the MRF system 600 may selectively adapt both operations during an MR procedure. In some implementations, the RF antennas 650 employs separate RF transmission and reception coils. Similarly, the RF antennas 650 may be controlled at least in part by a set of RF transmission units 660.

In some implementations, a control computer 670 controls some or all of the field magnet supply 620, the gradient coils supply 640, and/or the RF transmission units 660. In further implementations, the control computer 670 is further programmed to control an MR device such as MRF processing device 500. In other implementations, control computer 670 is or includes elements of MRF processing device 500. Conventionally, the MRF system 600 employs the MR signals received from the RF antennas 650 to generate an MRF image, and thus may be subject to a transformation process. In some implementations, the transformation process is or is akin to a two dimensional fast Fourier transform (FFT) that generates pixilated image data. Depending on the implementation an image computer 680 may perform the transformation. In other implementations, another, similar processing device performs the image transformation. Depending on the implementation, the display 690 may then display the image data. In some implementations, the display 690 may display some or all of the plots described with regard to FIGS. 1-9 above. For example, the display 690 may display any of the images, plots, etc. from FIGS. 3-9.

Fingerprinting apparatus 699 facilitates the unconventional techniques for MR image reconstruction and denoising as described herein. Further, the fingerprinting apparatus 699 facilitates the construction of images from MR signals received from the RF antennas 650. As such, the RF energy applied to an object by system 600 need not be constrained to produce signals with substantially constant amplitudes or phases. Instead, fingerprinting apparatus 699 facilitates matching received signals to known signals for which a reconstruction parameter, relaxation parameter, or other information is already available.

While FIG. 11 illustrates an example MRF system 600 that includes various components connected in various ways, one skilled in the art will appreciate that other MR systems may include other components connected in other ways.

In the foregoing specification, specific examples have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings. Additionally, the described embodiments/examples/implementations should not be interpreted as mutually exclusive, and should instead be understood as potentially combinable if such combinations are permissive in any way. In other words, any feature disclosed in any of the aforementioned embodiments/examples/implementations may be included in any of the other aforementioned embodiments/examples/implementations.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover, in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some examples may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

Moreover, the patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

What is claimed:

1. A method for synthetic late gadolinium enhancement imaging, the method comprising:
   receiving, by one or more processors, magnetic resonance fingerprinting (MRF) image data of a subject from a scanning device and obtaining, from the MRF image data, a $T_1$ tissue property map and a $T_2$ tissue property map co-registered with the $T_1$ tissue property map;
   identifying, using the one or more processors, a plurality of regions of interest in the MRF image data, the plurality of regions of interest comprising at least one myocardium region and a blood region;
   determining, by the one or more processors, $T_1$ and $T_2$ values for each of the plurality of regions of interest;
   determining, by the one or more processors and based on the $T_1$ and $T_2$ values for the plurality of regions of interest, a plurality of different sets of pulse sequence parameters, each set of pulse sequence parameters being configured to correspond to a different image contrast condition; and
   generating, by the one or more processors, a different contrast image for each of the different sets of pulse sequence parameters, wherein at least one contrast image is a synthetic bright-blood LGE image, at least one contrast image is a synthetic dark-blood/gray-blood LGE image, and at least one contrast image is a synthetic LGE image generated by numerically optimizing a contrast between different tissue types from among the plurality of regions of interest.

2. The method of claim 1, wherein the myocardium region is viable myocardium tissue region.

3. The method of claim 1, wherein the myocardium region is a myocardial fibrosis region, infarction region or scar tissue region.

4. The method of claim 1, wherein the plurality of regions of interest comprises a viable myocardium tissue region and a myocardial fibrosis region, infarction region or scar tissue region.

5. The method of claim 1, wherein determining the $T_1$ and $T_2$ values for each of the plurality of regions of interest comprises: determining the $T_1$ and $T_2$ values from measured $T_1$ and $T_2$ values in the $T_1$ tissue property map and the $T_2$ tissue property map, respectively.

6. The method of claim 1, wherein the myocardium region is a myocardial fibrosis region, infarction region or scar tissue region, and wherein determining the $T_1$ and $T_2$ values for the myocardium region comprises: determining the $T_1$ and $T_2$ values from measured $T_1$ and $T_2$ values in the $T_1$ tissue property map and the $T_2$ tissue property map, respectively.

7. The method of claim 1, wherein the plurality of regions of interest comprises a viable myocardium tissue region and a myocardial fibrosis region, infarction region or scar tissue region, and wherein determining the $T_1$ and $T_2$ values for the myocardium region comprises setting the $T_1$ value for the myocardium region to that of the $T_1$ value determined for blood tissue and setting the $T_2$ value for the myocardium region to that of the $T_2$ value determined for viable myocardium tissue.

8. The method of claim 1, wherein generating the synthetic bright-blood LGE image comprises calculating, using the $T_1$ property map, a synthetic phase sensitive inversion recovery (PSIR) image according to:

$$S_{PSIR} = 1 - 2e^{-\frac{TI}{T_1}} \quad \text{(Eq. 1)}$$

or
calculating magnitude inversion recovery images according to:

$$S_{MAG} = |S_{PSIR}| \quad \text{(Eq. 2)}$$

where TI is inversion time determined based on the $T_1$ value from one of the plurality of regions selected to null a corresponding tissue type, wherein the tissue type is selected from the group consisting of viable myocardium, blood, and myocardial fibrosis, infarction, or scar tissue.

9. The method of claim 8, wherein the synthetic bright-blood LGE image is generated from an inversion time, TI, corresponding to null signal for blood.

10. The method of claim 8, wherein the synthetic bright-blood LGE image is generated from an inversion time, TI, corresponding to null signal for viable myocardium.

11. The method of claim 1, wherein the synthetic dark-blood/gray-blood LGE image is a synthetic $T_2$-prepared phase sensitive inversion recovery (PSIR) sequence image.

12. The method of claim 11, wherein generating the synthetic $T_2$-prepared PSIR sequence image comprises:
    selecting a value for $\delta$, where $\delta$ is a parameter determining a level of blood signal suppression compared to viable myocardium, with $\delta<0$ resulting in blood having a lower signal intensity than viable myocardium and $\delta>0$ resulting in the blood having a higher signal intensity than viable myocardium;
    using $T_1$ and $T_2$ values obtained for each of the plurality of regions of interest, determining an inversion time, TI, and a T2 prep duration, $TE_{T2P}$, that satisfy optimization expression:

$$\max_{TI, TE_{T2P}} |M_z^{myo} - M_z^{scar}| + |M_z^{blood} - M_z^{scar}|$$

$$s.t. M_z^{blood} - M_z^{myo} - \delta < 0$$

where $M_z$ is longitudinal magnetization; and
for every pixel in the $T_1$ tissue map and the $T_2$ tissue map, performing a Bloch equation simulation of a $T_2$-prepared inversion recovery sequence using the determined TI and $TE_{T2P}$, wherein the output of the Bloch equation simulation is the synthetic dark-blood/gray-blood LGE image.

13. The method of claim 12, wherein the δ is selected to generate a synthetic dark-blood LGE image.

14. The method of claim 12, wherein the δ is selected to generate a synthetic gray-blood LGE image.

15. The method of claim 1, wherein the pulse sequence parameters comprise flip angle, radiofrequency (RF) phase, and time to repetition (TR), the method further comprising:
   determining a variable-length sequence of flip angles, RF phases, and TRs that maximally separate longitudinal magnetization values between different tissue types; and
   generating the synthetic LGE image by performing a Bloch equation simulation on the flip angles, RF phases, and TRs and on the $T_1$ and $T_2$ values for the different tissue types.

16. The method of claim 15, wherein the synthetic LGE image is generated from the flip angles, the TRs, and the RF phases determined by:
   selecting a value for n as a number of RF pulses in a contrast image simulation;
   randomly initializing a pulse sequence of n flip angles (α) between 0-360°, RF phases (ψ) between 0-360°, and repetition times (TR) between 0-500 ms for n RF pulses, where the flip angles, TRs, and RF phases are denoted as $\theta=\{\alpha_1, \psi_1, TR_1, \alpha_2, \psi_2, TR_2, \ldots a_n, \psi_n, TR_n\}$; and
   performing a numerical optimization on the flip angles and TRs to minimize a cost function $f(\theta)$.

17. The method of claim 16, wherein the cost function $f(\theta)$ is:

$$f(\theta) = \frac{\lambda_1}{|M_z^{scar}(n) - M_z^{blood}(n)|} + \frac{\lambda_2}{|M_z^{scar}(n) - M_z^{myo}(n)|} + \frac{\lambda_3}{|M_z^{myo}(n) - M_z^{blood}(n)|} \quad \text{(Eq. 5)}$$

$$\min_\theta f(\theta) \text{ s.t. } M_z^{myo} \leq M_z^{blood} \leq M_z^{scar} \quad \text{(Eq. 6)}$$

wherein where $M_z$ is longitudinal magnetization and wherein $\lambda_1$, $\lambda_2$, and $\lambda_3$ and tunable parameters.

18. A non-transitory computer-readable storage medium storing executable instructions that, when executed by a processor, cause a computer to:
   receive magnetic resonance fingerprinting (MRF) image data of a subject from a scanning device and obtaining, from the MRF image data, a $T_1$ tissue property map and a $T_2$ tissue property map co-registered with the $T_1$ tissue property map;
   identify a plurality of regions of interest in the MRF image data, the plurality of regions of interest comprising at least one myocardium region and a blood region;
   determine $T_1$ and $T_2$ values for each of the plurality of regions of interest;
   determine, based on the $T_1$ and $T_2$ values for the plurality of regions of interest, a plurality of different sets of pulse sequence parameters, each set of pulse sequence parameters being configured to correspond to a different image contrast condition; and
   generate a different contrast image for each of the different sets of pulse sequence parameters, wherein at least one contrast image is a synthetic bright-blood LGE image, at least one contrast image is a synthetic dark-blood/gray-blood LGE image, and at least one contrast image a synthetic LGE image generated by numerically optimizing a contrast between different tissue types from among the plurality of regions of interest.

19. The non-transitory computer-readable storage medium of claim 18, storing executable instructions to generate the synthetic bright-blood LGE image that, when executed, cause a computer to calculate, using the $T_1$ property map, a synthetic phase sensitive inversion recovery (PSIR) image according to:

$$S_{PSIR} = 1 - 2e^{-\frac{TI}{T_1}} \quad \text{(Eq. 1)}$$

or
calculate magnitude inversion recovery images according to:

$$S_{MAG} = |S_{PSIR}| \quad \text{(Eq. 2)}$$

where TI is inversion time determined based on the $T_1$ value from one of the plurality of regions selected to null a corresponding tissue type, wherein the tissue type is selected from the group consisting of viable myocardium, blood, and myocardial fibrosis, infarction, or scar tissue.

20. The non-transitory computer-readable storage medium of claim 18, storing executable instructions to generate the synthetic dark-blood/gray-blood LGE image as a synthetic $T_2$-prepared phase sensitive inversion recovery (PSIR) sequence image that, when executed, cause a computer to:
   select a value for δ, where δ is a parameter determining a level of blood signal suppression compared to viable myocardium, with δ<0 resulting in blood having a lower signal intensity than viable myocardium and δ>0 resulting in the blood having a higher signal intensity than viable myocardium;
   using $T_1$ and $T_2$ values obtained for each of the plurality of regions of interest, determine an inversion time, TI, and a T2 prep duration, $TE_{T2P}$, that satisfy optimization expression:

$$\max_{TI, TE_{T2P}} |M_z^{myo} - M_z^{scar}| + |M_z^{blood} - M_z^{scar}|$$

$$s.t. M_z^{blood} - M_z^{myo} - \delta < 0$$

where $M_z$ is longitudinal magnetization; and
   for every pixel in the $T_1$ tissue map and the $T_2$ tissue map, perform a Bloch equation simulation of a $T_2$-prepared inversion recovery sequence using the determined TI and $TE_{T2P}$, wherein the output of the Bloch equation simulation is the synthetic dark-blood/gray-blood LGE image.

21. The non-transitory computer-readable storage medium of claim 18, storing further executable instructions that, when executed, cause a computer to:
   determine a variable-length sequence of flip angles, radiofrequency (RF) phases, and time to repetition (TRs) that maximally separate longitudinal magnetization values between different tissue types; and generate the synthetic LGE image by performing a Bloch equation simulation on the flip angles, RF phases, and TRs and on the $T_1$ and $T_2$ values for the different tissue types.

22. A computing system for magnetic resonance imaging (MRI) post late gadolinium enhancement (LGE) contrast, the system comprising:
one or more processors;
a tissue map analyzer application configured to be executed by the one or more processors:
receive magnetic resonance fingerprinting (MRF) image data of a subject from a scanning device and obtain, from the MRF image data, a $T_1$ tissue property map and a $T_2$ tissue property map co-registered with the $T_1$ tissue property map; and
identify a plurality of regions of interest in the MRF image data, the plurality of regions of interest comprising at least one myocardium region and a blood region; and a synthetic LGE image generator application configured to be executed by the one or more processors:
determine $T_1$ and $T_2$ values for each of the plurality of regions of interest;
determine, based on the $T_1$ and $T_2$ values for the plurality of regions of interest, a plurality of different sets of pulse sequence parameters, each set of pulse sequence parameters being configured to correspond to a different image contrast condition; and
generate a different contrast image for each of the different sets of pulse sequence parameters, wherein at least one contrast image is a synthetic bright-blood LGE image at least one contrast image is a synthetic dark-blood/gray-blood LGE image, and at least one contrast image a synthetic LGE image generated by numerically optimizing a contrast between different tissue types from among the plurality of regions of interest.

* * * * *